US008034083B2

(12) United States Patent
Abdelgany et al.

(10) Patent No.: US 8,034,083 B2
(45) Date of Patent: Oct. 11, 2011

(54) ARTIFICIAL LIGAMENT ASSEMBLY

(75) Inventors: Mahmoud F. Abdelgany, Rockaway, NJ (US); YoungHoon Oh, Montville, NJ (US)

(73) Assignee: Custom Spine, Inc., Parsippany, NJ (US)

( * ) Notice: Subject to any disclaimer, the term of this patent is extended or adjusted under 35 U.S.C. 154(b) by 718 days.

(21) Appl. No.: 12/113,471

(22) Filed: May 1, 2008

(65) Prior Publication Data
US 2009/0275981 A1 Nov. 5, 2009

(51) Int. Cl.
*A61B 17/70* (2006.01)

(52) U.S. Cl. ........ 606/257; 606/246; 606/251; 606/254; 606/259; 623/17.11; 623/17.12; 623/13.11

(58) Field of Classification Search .................. 606/246, 606/248, 254–257, 261, 263, 264–278; 623/13.11, 623/13.12, 13.14, 13.15, 13.16, 17.12
See application file for complete search history.

(56) References Cited

U.S. PATENT DOCUMENTS

| | | | |
|---|---|---|---|
| 3,971,134 A | 7/1976 | Bokros | |
| D245,516 S | 8/1977 | Treace | |
| 4,246,660 A | 1/1981 | Wevers | |
| 4,795,466 A | 1/1989 | Stuhmer et al. | |
| 5,024,669 A | 6/1991 | Peterson et al. | |
| 5,092,887 A | 3/1992 | Gendler | |
| 5,116,372 A | 5/1992 | Laboureau | |
| 5,180,393 A | 1/1993 | Commarmond | |
| 5,376,119 A | 12/1994 | Zimmermann et al. | |
| 5,425,767 A | 6/1995 | Steininger et al. | |
| 5,468,241 A | 11/1995 | Metz-Stavenhagen et al. | |
| 5,800,543 A | 9/1998 | McLeod et al. | |
| 5,890,902 A | 4/1999 | Sapian | |
| 5,993,486 A | 11/1999 | Tomatsu | |
| 6,585,769 B1 | 7/2003 | Muhanna et al. | |
| 7,041,136 B2 | 5/2006 | Goble et al. | |
| 7,074,237 B2 | 7/2006 | Goble et al. | |
| 7,087,084 B2 | 8/2006 | Reiley | |
| 7,090,698 B2 | 8/2006 | Goble et al. | |
| 7,115,142 B2 | 10/2006 | Muhanna et al. | |
| 7,290,347 B2 | 11/2007 | Augostino et al. | |
| 7,344,539 B2 | 3/2008 | Serhan et al. | |
| 7,776,075 B2 * | 8/2010 | Bruneau et al. | 606/279 |
| 7,867,256 B2 * | 1/2011 | Schlaepfer | 606/257 |
| 2005/0065514 A1 * | 3/2005 | Studer | 606/61 |
| 2005/0085815 A1 | 4/2005 | Harms et al. | |
| 2005/0203517 A1 * | 9/2005 | Jahng et al. | 606/61 |
| 2005/0261686 A1 * | 11/2005 | Paul | 606/61 |
| 2005/0288672 A1 * | 12/2005 | Ferree | 606/61 |
| 2006/0036240 A1 * | 2/2006 | Colleran et al. | 606/61 |
| 2006/0041259 A1 * | 2/2006 | Paul et al. | 606/61 |

(Continued)

*Primary Examiner* — Eduardo C Robert
*Assistant Examiner* — Michelle C Eckman
(74) *Attorney, Agent, or Firm* — Rahman LLC

(57) ABSTRACT

An artificial ligament assembly for spinal stabilization includes an outer hollow elastic longitudinal member, a rigid inner member, a bone anchor mechanism, a bone anchor, and a buffered space. The artificial ligament assembly further includes a clamp that controls a torsional motion of the outer hollow elastic longitudinal member with respect to the bone anchor mechanism. The outer hollow elastic longitudinal member is at least as long as the inner rigid member. The rigid inner member is configured in a substantially same shape as the outer hollow elastic longitudinal member. The bone anchor mechanism is coupled to the outer hollow elastic longitudinal member. The bone anchor connector may further include an insert end. The bone anchor is coupled to the bone anchor mechanism. The buffered space allows any of a compression and an extension of the bone anchor mechanism inside the outer hollow elastic longitudinal member.

20 Claims, 5 Drawing Sheets

U.S. PATENT DOCUMENTS

| | | |
|---|---|---|
| 2006/0084984 A1* | 4/2006 | Kim .................................. 606/61 |
| 2006/0229612 A1* | 10/2006 | Rothman et al. ................. 606/61 |
| 2006/0264937 A1 | 11/2006 | White |
| 2006/0265074 A1* | 11/2006 | Krishna et al. ............. 623/17.15 |
| 2007/0005137 A1 | 1/2007 | Kwak |
| 2007/0049937 A1* | 3/2007 | Matthis et al. .................. 606/61 |
| 2007/0233073 A1* | 10/2007 | Wisnewski et al. ............. 606/61 |
| 2008/0021459 A1* | 1/2008 | Lim .................................. 606/61 |
| 2009/0048631 A1* | 2/2009 | Bhatnagar et al. ............. 606/246 |
| 2009/0099608 A1* | 4/2009 | Szczesny ....................... 606/257 |
| 2009/0163953 A1* | 6/2009 | Biedermann et al. ......... 606/254 |
| 2010/0069964 A1* | 3/2010 | Lechmann ..................... 606/278 |
| 2010/0274287 A1* | 10/2010 | Rouleau et al. ............... 606/255 |
| 2010/0274288 A1* | 10/2010 | Prevost et al. ................. 606/257 |

* cited by examiner

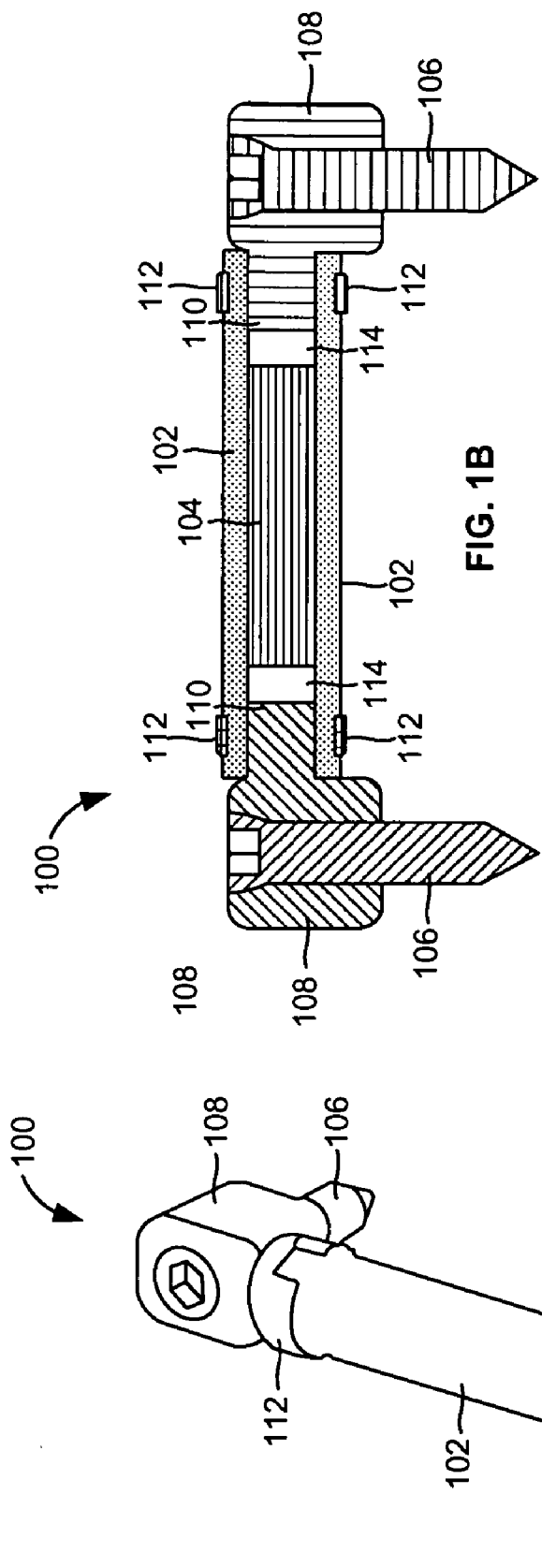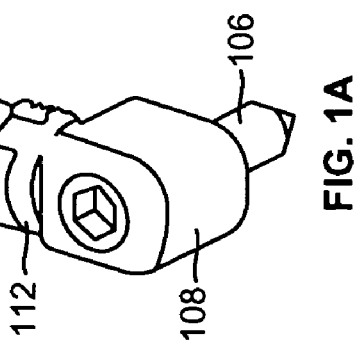

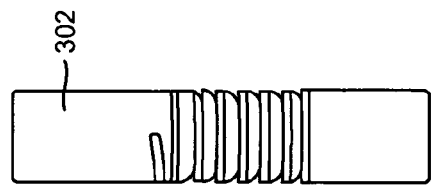
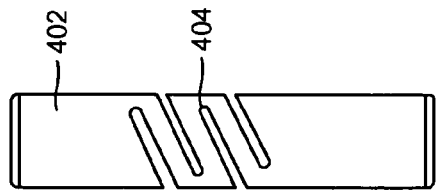
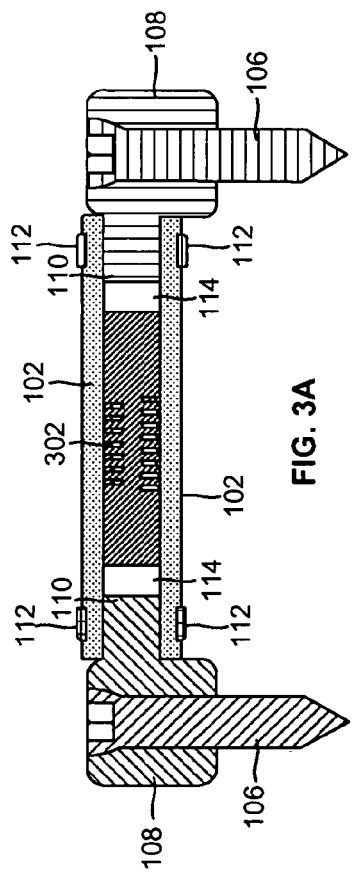
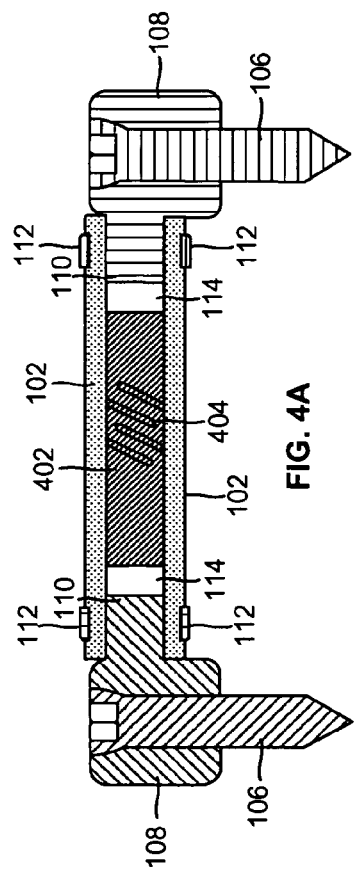

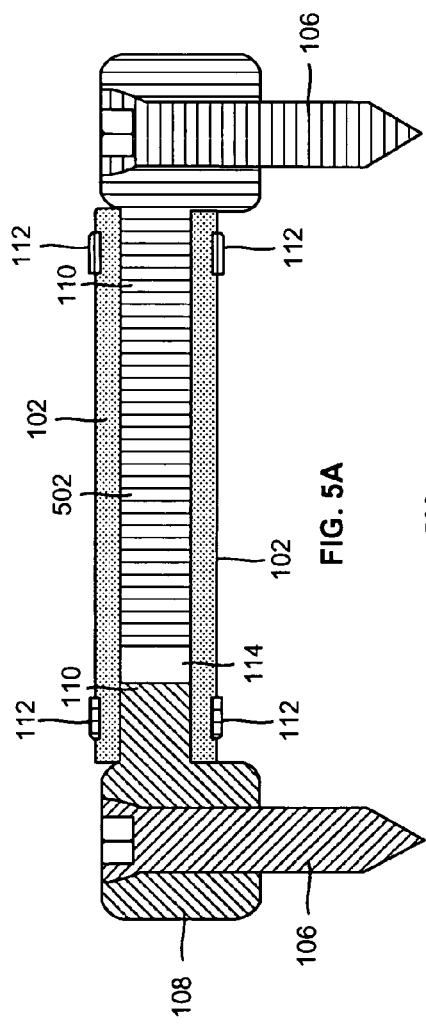
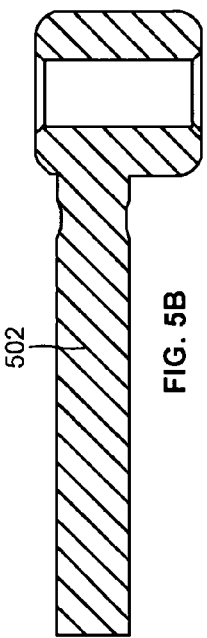
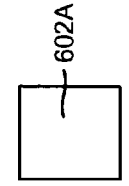
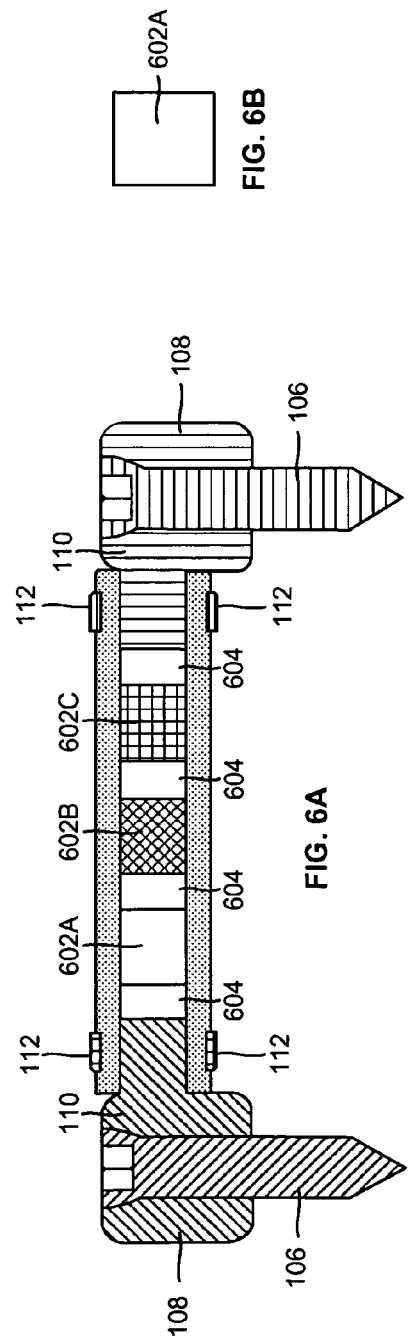

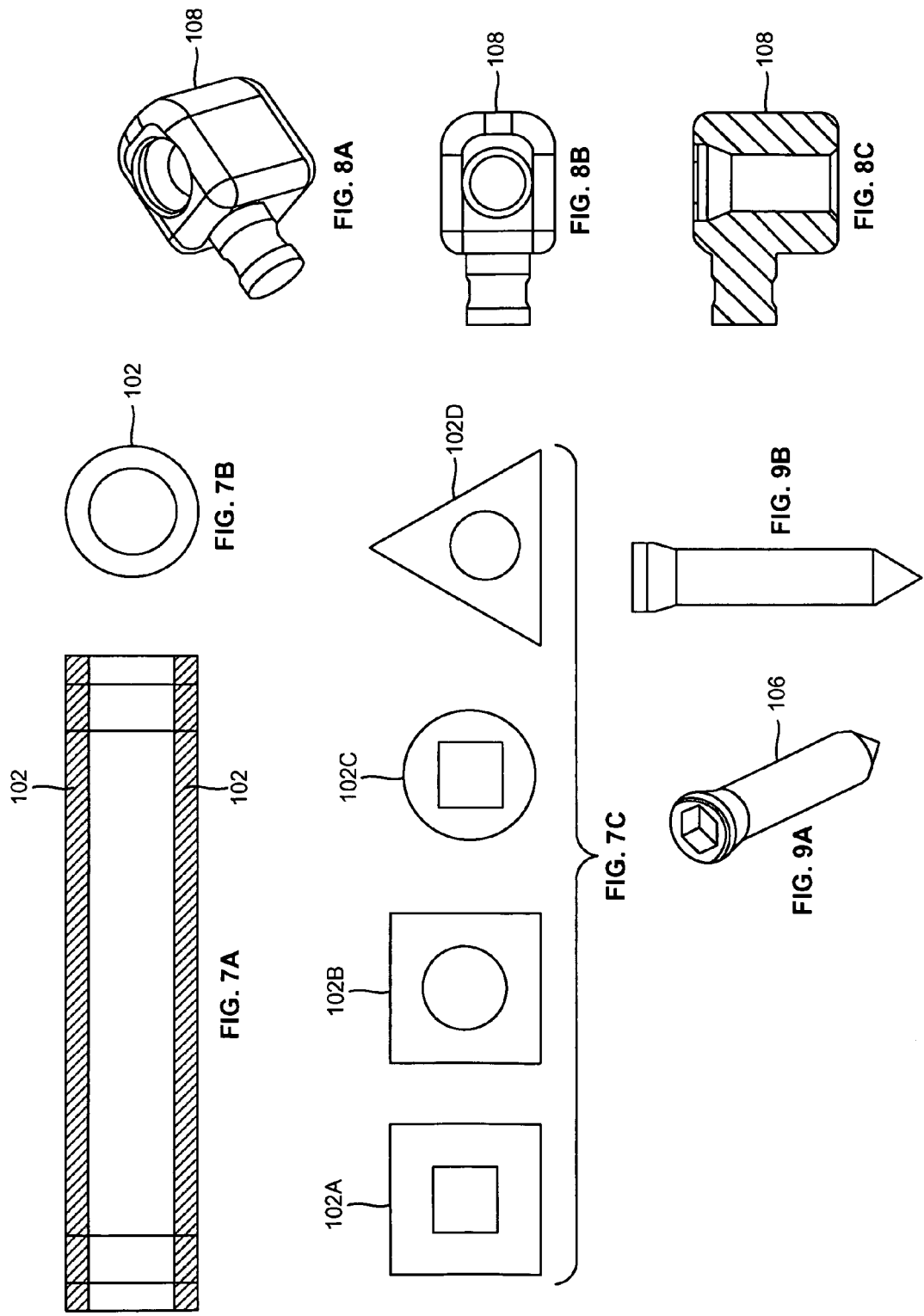

ARTIFICIAL LIGAMENT ASSEMBLY

BACKGROUND

1. Technical Field

The embodiments herein generally relate to spinal stabilization devices, and more particularly to an artificial ligament assembly used for spinal stabilization.

2. Description of the Related Art

Ligaments are bands of tough, elastic, fibrous tissue that connect bones together at joints so that the joints can move. Ligaments are found at all of the joints of the skeleton (e.g., as in knees, head and neck, thorax, elbow, wrist etc.). Moreover, ligaments act to limit the motion of bones relative to each other, thus providing stability to the joints. Bone joints are vulnerable to injury for anyone involved in strenuous activities. Ligaments are more susceptible to being torn with violent twisting forces. Due to abrupt or progressive stress, a ligament is susceptible to tearing.

When a ligament is torn, it can either be repaired or replaced. Generally, repairing heals a torn ligament poorly; hence the ligament must be replaced. Most replacements come from connective tissues in a patient's own body (e.g., a knee tendon). Rehabilitation and return to full strength can take one to two years or more. To reduce rehabilitation time and provide greater strength, artificial ligaments are used. Artificial ligaments are required because the natural ligaments heal slowly and are often damaged irreparably. Various types of artificial ligament devices have been developed.

Most of the artificial ligament devices provide required tension support which is usually greater than necessary torsion limitation. The torsional movement is excessively limited (e.g., fully rigid) or has a minimal torsional micro-motion which is based solely on the material and/or geometry of the device (e.g., plate). Generally, these artificial ligament devices do not provide compression load-bearing support as well. Compression is not limited (e.g., exceedingly flexible), and there is non-load bearing with macro-motion which is based solely on the material and/or geometry (e.g., elastic band).

Also, these artificial ligament devices generally do not have a torsion limitation, and typically do not provide a controlled torsional range of motion with the skeletal body. Also, these devices generally do not provide compression and would not benefit for the spinal stabilization due to excessive flexion and extension. Furthermore, these devices generally do not provide controlled stabilization to a patient with spinal pathologies and do not assist in the restoration of natural ligamentous support.

SUMMARY

In view of the foregoing, an embodiment herein provides an artificial ligament assembly for spinal stabilization. The artificial ligament assembly includes an outer hollow elastic longitudinal member, a rigid inner member, a bone anchor mechanism, a bone anchor, and a buffered space. The artificial ligament assembly further includes a clamp that controls a torsional motion of the outer hollow elastic longitudinal member with respect to the bone anchor mechanism. Preferably, the outer hollow elastic longitudinal member is at least as long as the inner rigid member. Preferably, the rigid inner member is configured in a substantially same shape as the outer hollow elastic longitudinal member.

The rigid inner member fits inside the outer hollow elastic longitudinal member. The inner rigid member may include any of concentric rings, symmetric opposing slots, and spring mechanisms. The bone anchor mechanism is coupled to the outer hollow elastic longitudinal member. The bone anchor mechanism may further include a bone anchor connector positioned at least partially inside the outer hollow elastic longitudinal member. The bone anchor connector may further include an insert end.

A first one of the bone anchor connector may include a first insert end having a first length and a second one of the bone anchor connector may include a second insert end having a second length longer than the first length. The bone anchor mechanism may be one continuous structure. The bone anchor mechanism may include any of a monoaxial member, a polyaxial member, a medialised polyaxial member, a medialised monoaxial member, a dynamic polyaxial member, a post, and a staple structure. The bone anchor mechanism may be positioned on any of an anterior, a posterior, and a lateral side of a vertebral body. The bone anchor is coupled to the bone anchor mechanism. The buffered space is between the rigid inner member and the bone anchor mechanism. The buffered space allows any of a compression and an extension of the bone anchor mechanism inside the outer hollow elastic longitudinal member.

In another aspect, an apparatus for stabilizing a vertebral body includes a substantially elongated outer hollow elastic longitudinal member, a rigid inner member, a pair of opposed bone anchor connector(s), a bone anchor, a buffered space and a torsion control mechanism. The rigid inner member is positioned inside the outer hollow elastic longitudinal member. The outer hollow flexible longitudinal member and the rigid inner member may include any of a circular, an oval, a rectangular, a square, and a triangular configuration. The bone anchor connectors are coupled to the outer hollow elastic longitudinal member. Each of the bone anchor connectors may include an opening dimensioned and configured to receive the bone anchor. Each of the bone anchor connectors may include an insert end that is elongated to a length shorter than that of the outer hollow flexible longitudinal member.

The bone anchor is inserted into the vertebral body and is coupled to each of the bone anchor connectors. The buffered space may be between the rigid inner member and the bone anchor mechanism. The buffered space allows for a bilateral movement of each of the bone anchor connectors inside the outer hollow elastic longitudinal member. The torsion control mechanism is coupled to the outer hollow flexible longitudinal member that controls a torsional motion of the bone anchor connectors with respect to a longitudinal axis of the outer hollow flexible longitudinal member.

In another aspect, an apparatus that functions as a natural ligament includes a bone anchor, a bone anchor connector, an outer hollow flexible longitudinal member, an inner member, a clamp and a buffered space. The bone anchor connector is coupled to the bone anchor. The bone anchor connector includes an insert end. The bone anchor connector may include an opening which is dimensioned and configured to receive the bone anchor. The outer hollow flexible longitudinal member is an elastic material that surrounds the insert end of the bone anchor connector.

The inner member is positioned inside the outer hollow flexible longitudinal member. The inner member may resist a compression of the bone anchor connector within the hollow flexible longitudinal member. The inner member may include any of a rigid member, an elongated bone anchor connector, and a spring-like member. The inner member may also include a plurality of rigid members spaced apart from one another and positioned within the outer hollow flexible longitudinal member. The inner member may further include at least one of concentric rings, symmetric opposing slots, and a spring-shape mechanism.

Preferably, the clamp is fastened around the outer hollow flexible longitudinal member. The clamp controls a torsional motion of the bone anchor. The buffered space is inside the hollow flexible longitudinal member and is positioned adjacent to the insert end of the bone anchor connector. The buffered space allows a compression and an extension of the bone anchor connector within the hollow flexible longitudinal member.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which:

FIG. 1A illustrates a perspective view of an artificial ligament assembly according to an embodiment herein;

FIG. 1B illustrates a cross-sectional view of the artificial ligament assembly of FIG. 1A according to a first embodiment herein;

FIG. 2A illustrates an isolated view of the inner member of FIG. 1B according to the first embodiment herein;

FIG. 2B illustrates a cross-sectional view of the inner member of FIG. 1B according to the first embodiment herein;

FIG. 3A illustrates a cross-sectional view of the artificial ligament assembly of FIG. 1A according to a second embodiment herein;

FIG. 3B illustrates an isolated view of the spring-like inner member of FIG. 3A according to the second embodiment herein;

FIG. 4A illustrates a cross-sectional view of the artificial ligament assembly of FIG. 1A according to a third embodiment herein;

FIG. 4B illustrates an isolated view of the inner member with the cuts of FIG. 4A according to the third embodiment herein;

FIG. 5A illustrates a cross-sectional view of the artificial ligament assembly of FIG. 1A according to a fourth embodiment herein;

FIG. 5B illustrates an isolated view of the elongated bone anchor connector of FIG. 5A according to the fourth embodiment herein;

FIG. 6A illustrates a cross-sectional view of the artificial ligament assembly of FIG. 1A according to a fifth embodiment herein;

FIG. 6B illustrates an isolated view of the inner member of FIG. 6A according to the fifth embodiment herein;

FIG. 7A illustrates a cross-sectional view of a cylindrical configuration of the outer hollow member of the artificial ligament assembly of FIG. 1A according to an embodiment herein;

FIG. 7B illustrates a cross-sectional view of the cylindrical configuration of the outer hollow member of FIG. 7A according to an embodiment herein;

FIG. 7C illustrates cross-sectional views of different alternative configurations of the outer hollow member of the artificial ligament assembly of FIG. 7A according to the embodiments herein;

FIG. 8A illustrates a perspective view of the bone anchor connector of the artificial ligament assembly of FIG. 1A according to an embodiment herein;

FIG. 8B illustrates a front view of the bone anchor connector of the artificial ligament assembly of FIG. 1A according to an embodiment herein;

FIG. 8C illustrates a cross-sectional view of the bone anchor connector of the artificial ligament assembly of FIG. 1A according to an embodiment herein;

FIG. 9A illustrates a perspective view of the bone anchor of the artificial ligament assembly of FIG. 1A according to an embodiment herein;

FIG. 9B illustrates a front view of the bone anchor of the artificial ligament assembly of FIG. 1A according to an embodiment herein;

DETAILED DESCRIPTION OF PREFERRED EMBODIMENTS

Figure 11:
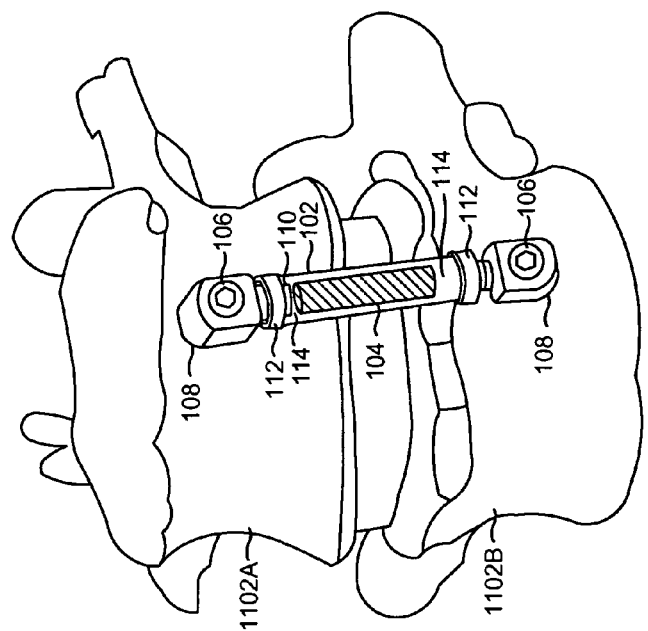
FIG. 11 illustrates a perspective view of the artificial ligament assembly of FIG. 1A inserted into two adjacent vertebrae according to the embodiments herein.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The embodiments herein provide a new and improved artificial ligament assembly to support tension and compression loading on either the anterior, posterior, or lateral side of the vertebral body, which limits torsion on the vertebral body in a controlled manner for spinal column stabilization. The artificial ligament assembly provides controlled stabilization to a patient with spinal pathologies requiring restoration of natural ligamentous support. The artificial ligaments assembly provides a controlled torsional range of motion with the vertebral body. In addition, the artificial ligament assembly supports tension and compression loading on either the anterior, posterior, or lateral side of vertebral body. The assembly is dynamic to limit torsion on the vertebral body in a controlled manner, may be used as a stand-alone device, or in conjunction with anterior or posterior implants to support vertebral stabilization. Referring now to the drawings and more particularly to FIGS. 1A through 11 where similar reference characters denote corresponding features consistently throughout the figures, there are shown preferred embodiments.

FIG. 1A illustrates a perspective view of an artificial ligament assembly 100, according to an embodiment herein. The artificial ligament assembly 100 includes an outer hollow member 102, a bone anchor 106, a bone anchor connector 108, and a clamp 112. The outer hollow member 102 comprises a flexible, hollow structure made of an elastic material with properties similar to that of natural ligaments. For example, outer hollow member 102 may comprise any of biocompatible polycarbonate urethane, polyurethane, polyetheretherketone, ceramic-coated silicon, and Salubria® biomaterial available from Salumedia, Inc., Georgia, USA, etc., for example. Bone anchor 106, bone anchor connector 108, and clamp 112 may comprise any of biocompatible titanium alloy, stainless steel, polyetheretherketone, etc., for example. In one embodiment, the outer hollow member 102 comprises a longitudinal tube-like structure. The bone anchor 106 may be embodied as a screw used for connecting to the bones. Alternatively, the bone anchor 106 may be configured as a hook. The bone anchor 106 is held in position by the bone anchor connector 108.

The bone anchor connector 108 is a connector which connects the bone anchor 106 to the outer hollow member 102. The bone anchor connector 108 is inserted into the outer hollow member 102. The clamp 112 is a circular ring attached to the outer hollow member 102. The clamp 112 is used for fixing the outer hollow member 102 to an inner member (not shown) and the bone anchor connector 108 in position. FIG. 1B illustrates a cross-sectional view of the artificial ligament assembly 100 of FIG. 1A according to a first embodiment herein. The artificial ligament assembly 100 includes the outer hollow member 102, an inner member 104, the bone anchor 106, the bone anchor connector 108, the clamp 112, and a buffer 114. The buffer 114 may comprise an empty space (e.g., air) or may be filled with a liquid (such as the patient's blood, for example).

The bone anchor connector 108 includes an insert end 110. The inner member 104 is a stabilizing rigid member that fits inside the outer hollow member 102 and is spaced apart from the ends of the bone anchors 106 and the bone anchor connector(s) 108. The insert end 110 of the bone anchor connector 108 is an extension of the bone anchor connector 108 which is inserted in the interior of the outer hollow member 102. The insert end 110 of the bone anchor connector 108 is the end of the bone anchor connector 108 connected to the inner member 104 through the buffer 114.

The buffer 114 is a vacuum formed between the insert end 110 of the bone anchor connector 108 and the inner member 104 inside the outer hollow member 102. The inner member 104 is inserted in the flexible outer hollow member 102 such that there are spaces between the rigid inner member 102 and the bone anchor connector(s) 108. The buffer 114 may allow for the compression/extension of the bone anchor connector (s) 108 into the flexible outer hollow member 102. The buffer 114 serves to have controlled motion in both lateral directions.

FIG. 2A illustrates an isolated view of the inner member 104 of FIG. 1B, according to a first embodiment herein. The inner member 104 is made of a material more rigid than the outer hollow member 102. For example, the inner member 104 may comprise any of biocompatible titanium alloy, stainless steel, and polyetheretherketone etc. The inner member 104 is shorter than the outer hollow member 102. The longitudinal shape of the inner member 104 has the shape of the outer hollow member 102. FIG. 2B illustrates a cross-sectional view of the inner member 104 of FIG. 1B according to the first embodiment herein. The inner member 104 may allow for some flexion and may be configured in any shape (e.g., not only cylindrical).

The inner member 104 may be configured to resist compression and allow the assembly 100 to dampen loading, thereby shielding the bone from undue stress. This occurs by limiting the distance between the bone anchors 106 by controlling the compression/extension of the bone anchor(s) (e.g., the bone anchor 106 of FIG. 1B) with respect to one another. FIG. 3A illustrates a sectional view of the artificial ligament assembly 100 of FIG. 1A having a spring-like inner member 302 according to a second embodiment herein. The spring-like inner member 302 is a rigid member that fits inside the outer hollow member 102 and is spaced apart from the ends of the bone anchor(s) 106 and the bone anchor connector(s) 108.

In one embodiment, the inner member 104 may be of any shape and configuration and may also contain concentric rings of various geometries, symmetric opposing slots, or it may be embodied as a spring-shape mechanism. FIG. 3B illustrates an isolated view of the spring-like inner member 302 of FIG. 3A according to the second embodiment herein. The spring-like inner member 302 is made of a material more rigid than the outer hollow member 102. In one embodiment, the spring-like inner member 302 is formed of titanium to further control the compression/extension of the bone anchor (s) 106 when they rest against the spring-like inner member 302.

FIG. 4A illustrates a cross-sectional view of the artificial ligament assembly 100 of FIG. 1A having an inner member 402 with cuts 404 according to a third embodiment herein. The inner member 402 is made of a rigid material such as biocompatible titanium alloy, stainless steel, polyetheretherketone, etc., for example. The inner member 402 is shorter than the outer hollow member 102. FIG. 4B illustrates an isolated view of the inner member 402 with cuts 404 according to the third embodiment herein. The cuts 404 in the inner member 402 are thread-like structures in the center portion of the spring-like inner member 302. The cuts 404 in the inner member 402 may allow flexion and spring resistance.

FIG. 5A illustrates a cross-sectional view of the artificial ligament assembly 100 of FIG. 1A having an elongated bone anchor connector 502 according to a fourth embodiment herein. The elongated bone anchor connector 502 is an extension of the insert end 110 of the bone anchor connector 108 of FIG. 1A that is inserted inside the outer hollow member 102. The elongated bone anchor connector 502 acts as the inner element (e.g., as the inner member 104 of FIG. 1A). The elongated bone anchor connector 502 is shorter than the outer hollow member 102. FIG. 5B illustrates an isolated view of the elongated bone anchor connector 502 of FIG. 5A according to the fourth embodiment herein.

In one embodiment, one of the two bone anchor connector (s) 108 is elongated to form the inner element. In another embodiment, both of the (the two) bone anchor connector(s) 108 are elongated to act as the inner element. FIG. 6A illustrates a cross-sectional view of the artificial ligament assembly 100 of FIG. 1A having multiple inner members 602A, 602B and 602C according to a fifth embodiment herein. In one embodiment, the inner member 602 may be inserted as a plurality of inner members (e.g., 602A, 602B, and 602C) inside the outer hollow member 102. The multiple inner members 602A, 602B, and 602C are separated by the buffered spaces 604 (e.g., empty spaces or liquid-filled) between them.

The buffered spaces 604 allow for the compression/extension of the bone anchor connector(s) 108 into the flexible outer hollow member 102. FIG. 6B illustrates an isolated view of the inner member 602A of FIG. 6A, according to the fifth embodiment herein. FIG. 7A illustrates a cross-sectional view of a cylindrical configuration of the outer hollow member 102 of the artificial ligament assembly 100 of FIG. 1A according to an embodiment herein. The outer hollow member 102 is a hollow longitudinal structure made of a flexible elastic material such as biocompatible polycarbonate urethane, polyurethane, polyetheretherketone, ceramic-coated silicon, Salubria® biomaterial available from Salumedia, Inc., Georgia, USA, etc. The outer hollow member 102 is attached to the bone anchors 106 and functions as ligaments in connecting the bones.

FIG. 7B, with reference to FIG. 7A, illustrates a cross-sectional view of the cylindrical configuration of the outer hollow member 102 of FIG. 1A according to an embodiment herein. FIG. 7C illustrates cross-sectional views of different alternative configurations 102A, 102B, 102C, and 102D of the outer hollow member 102 of the artificial ligament assembly 100 of FIG. 1A according to an embodiment herein. As shown, the outer hollow member 102 may have the configuration of a circle, an oval, a rectangle, a square, or a triangle, or other configurations that are not shown.

FIGS. 8A, 8B, and 8C illustrate a perspective view, a front view, and a cross-sectional view, respectively, of the bone anchor connector 108 of the artificial ligament assembly 100 of FIG. 1A according to an embodiment herein. The bone anchor connector(s) 108 is inserted into the outer hollow member 102 and connects the bone anchor(s) 106. In one embodiment, the bone anchor mechanism may be one part (i.e., the bone anchor 106 and the bone anchor connector 108 are a one-piece construct). In another embodiment, the bone anchor mechanism may be of two parts (i.e., the bone anchor 106 and the bone anchor connector 108 are two separate pieces).

FIGS. 9A and 9B illustrate a perspective view and a front view, respectively, of the bone anchor 106 of the artificial ligament assembly 100 of FIG. 1A according to an embodiment herein. The bone anchors 106 may be embodied as a screw used for connecting to the bones. The bottom of the bone anchors 106 is attached to the bone. The bone anchors 106 are held in position by the bone anchor connector(s) 108. In one embodiment, the bone anchors 106 may be a monoaxial member, a polyaxial member, a medialised monoaxial member, a medialised polyaxial member, a dynamic polyaxial member, post, or a staple structure. The bone anchors 106 may be placed on the anterior, posterior, or lateral side of the vertebral body.

Figure 10:
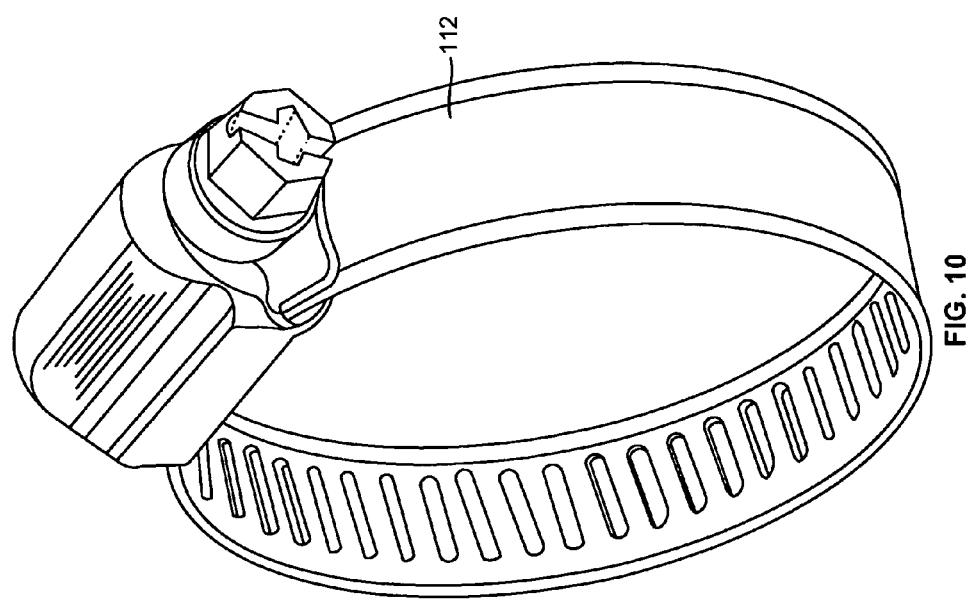
FIG. 10 illustrates a perspective view of the clamp of the bone joint assembly of FIG. 1A according to an embodiment herein.

FIG. 10 illustrates a perspective view of the clamp 112 of the bone joint assembly 100 of FIG. 1A according to an embodiment herein. The clamp 112 is configured, according to one embodiment, as a circular ring attached around the outer hollow member 102. The clamp 112 is used for fixing the outer hollow member 102 to the inner member 104 and the bone anchor connector 108 in position. The clamp 112 controls a torsional motion of the bone anchor 106 with respect to an axis of the outer hollow member 102.

FIG. 11 illustrates a cross-sectional view of the artificial ligament assembly 100 of FIG. 1A inserted into two adjacent vertebrae 1102A, 1102B according to an embodiment herein. For the implantation of the artificial ligament assembly 100 in the vertebrae 1102A, 1102B, initially, an area of implantation is surgically approached and an incision (not shown) is made over the two adjacent vertebrae 1102A, 1102B. After the incision has been made, the artificial ligament assembly 100 is positioned exactly over the incision of the two adjacent vertebrae 1102A, 1102B.

The outer hollow member 102 is an elastic material and functions as an artificial ligament in the joint of the vertebrae 1102A, 1102B. The inner member 104 may also include a plurality of rigid members spaced apart from one another and positioned within the outer hollow member 102. The inner member 104 may include any of a rigid member, an elongated bone anchor connector, and a spring-like member. The inner member 104 may further include at least one of concentric rings, a symmetric opposing slots, and a spring-shape mechanism. The inner member 102 may resist a compression of the bone anchor connector 108 within the outer hollow member 102 to provide a stability for a vertebral body 1102A, 1102B.

The bone anchor connectors 108 are connected to the outer hollow member 104. The bone anchor connector 108 has an opening dimensioned and configured to receive the bone anchor 106. The bone anchor connector 108 has the insert end 110 that is elongated to a length shorter than that of the outer hollow member 102. The bone anchor 106 is inserted into the vertebral body and connected to the bone anchor connectors 108. The bone anchor 106 may be embodied as a screw used for connecting to the bones 1102A, 1102B. Alternatively, the bone anchor 106 may be configured as a hook.

The two bone anchor(s) 106 are inserted into the incision of the two adjacent vertebrae 1102A, 1102B and tightened through an opening of the bone anchor connector 108. The bone anchor 106 is held in position by the bone anchor connector 108. The artificial ligament assembly 100 is implanted over the two adjacent vertebrae 1102A, 1102B along the axis of the outer hollow member 102 so as to make a joint between the two adjacent vertebrae 1102A, 1102B. The clamp 112 is embodied as a circular ring used for fixing the outer hollow member 102 to the inner member 104 and the bone anchor connector 108 in position. However, those skilled in the art would understand that other configurations for the clamp 112 are possible.

The clamp 112 is connected to the outer hollow member 102 and controls a torsional motion of the bone anchor connectors 108 with respect to a longitudinal axis of the outer hollow member 104. The buffer 114 is an empty space inside the outer hollow member 102 and is positioned adjacent to the insert end 110 of the bone anchor connector 108. The buffer 114 between the inner member 104 and the bone anchor connector 108 allows for a bilateral movement of each of the bone anchor connectors 108 inside the outer member 102. The buffer 114 allows any of a compression and an extension of the bone anchor connector 108 inside the outer hollow member 104, thus providing additional stability for the vertebral body.

The embodiments herein provide an artificial ligament assembly 100 that supports for spinal column stabilization. The artificial ligament assembly 100 provides a controlled stabilization to a patient with spinal pathologies requiring restoration of natural ligamentous support. The artificial ligament assembly 100 provides a controlled torsional range of motion with the vertebral body 1102A, 1102B. In addition, the artificial ligament assembly 100 supports tension and compression loading on either the anterior, posterior, or lateral side of vertebral body 1102A, 1102B. The artificial ligaments assembly 100 is dynamic to limit torsion on the vertebral body in a controlled manner, may be used as a standalone device, or in conjunction with anterior or posterior implants to support vertebral stabilization.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:

1. An artificial ligament assembly comprising: an outer hollow elastic longitudinal member comprising a first portion and a second portion, wherein said first and said second portion are significantly parallel to one another; a rigid inner member configured in a substantially same shape as said outer hollow elastic longitudinal member, wherein said rigid inner member fits inside said outer hollow elastic longitudinal member; at least one bone anchor mechanism directly coupled to said outer hollow elastic longitudinal member; at least one bone anchor directly coupled to said at least one bone anchor mechanism; and at least one buffered space between said rigid inner member and said bone anchor mechanism and further between said first portion and said second portion of said outer hollow elastic longitudinal member, wherein said at least one buffered space allows at least one of a compression and an extension of said bone anchor mechanism inside said outer hollow elastic longitudinal member, and wherein said at least one buffered space is filled with a liquid or air.

2. The artificial ligament assembly of claim 1, wherein said bone anchor mechanism comprises a bone anchor connector positioned at least partially inside said outer hollow elastic longitudinal member.

3. The artificial ligament assembly of claim 1, further comprising a clamp that controls a torsional motion of said outer hollow elastic longitudinal member with respect to said bone anchor mechanism.

4. The artificial ligament assembly of claim 1, wherein said outer hollow elastic longitudinal member is at least as long as said rigid inner member.

5. The artificial ligament assembly of claim 1, wherein said rigid inner member comprises at least one of concentric rings, symmetric opposing slots, and spring mechanisms.

6. The artificial ligament assembly of claim 2, wherein said bone anchor connector comprises an insert end, wherein a first one of said bone anchor connector comprises a first insert end having a first length, and wherein a second one of said bone anchor connector comprises a second insert end having a second length longer than said first length.

7. The artificial ligament assembly of claim 1, wherein each bone anchor mechanism comprises one continuous structure.

8. The artificial ligament assembly of claim 1, wherein said bone anchor mechanism comprises at least one of a monoaxial member, a polyaxial member, a medialised polyaxial member, a medialised monoaxial member, a dynamic polyaxial member, a post, and a staple structure.

9. The artificial ligament assembly of claim 1, wherein said bone anchor mechanism is positioned on at least one of an anterior, a posterior, and a lateral side of a vertebral body.

10. An apparatus for stabilizing a vertebral body comprising: a substantially elongated outer hollow elastic longitudinal member; a rigid inner member positioned inside said outer hollow elastic longitudinal member; a pair of opposed bone anchor connectors directly coupled to said outer hollow elastic longitudinal member; a bone anchor insertable into a vertebral body and directly coupled to each said opposed bone anchor connectors; at least one buffered space between said rigid inner member and said bone anchor connectors, wherein said at least one buffered space allows for bilateral movement of each said bone anchor connectors inside said outer hollow elastic longitudinal member, and wherein said at least one buffered space is filled with a liquid or air; and a torsion control mechanism coupled to said outer hollow flexible longitudinal member that controls a torsional motion of said pair of opposed bone anchor connectors with respect to a longitudinal axis of said outer hollow elastic longitudinal member.

11. The apparatus of claim 10, wherein each said bone anchor connector comprises an opening that receives said bone anchor.

12. The apparatus of claim 10, wherein each said bone anchor connector comprises an insert end that is elongated to a length shorter than that of said outer hollow elastic longitudinal member.

13. The apparatus of claim 10, wherein said outer hollow elastic longitudinal member and said rigid inner member comprise any a circular, oval, rectangular, square, and triangular configuration.

14. An apparatus that functions as a natural ligament, said apparatus comprising:
   a bone anchor;
   a bone anchor connector directly coupled to said bone anchor, wherein said bone anchor connector comprises an insert end;
   an outer hollow flexible longitudinal member comprising elastic material, wherein said outer hollow flexible longitudinal member surrounds, and is in direct contact with, said insert end of said bone anchor connector;
   an inner member positioned inside said outer hollow flexible longitudinal member;
   a clamp fastened around said outer hollow flexible longitudinal member, wherein said clamp controls a torsional motion of said bone anchor; and
   at least one buffered space inside said hollow flexible longitudinal member and positioned adjacent to said insert end of said bone anchor connector, wherein said buffered space allows compression and extension of said bone anchor connector within said hollow flexible longitudinal member, and wherein said at least one buffered space is filled with a fluid.

15. The apparatus of claim 14, wherein said bone anchor connector comprises an opening, wherein said opening receives said bone anchor.

16. The apparatus of claim 14, wherein said inner member resists compression of said bone anchor connector within said hollow flexible longitudinal member.

17. The apparatus of claim 16, wherein said inner member comprises any of a rigid member, an elongated bone anchor connector, and a spring-like member.

18. The apparatus of claim 14, wherein said inner member comprises a plurality of rigid members spaced apart from one another and positioned within said outer hollow flexible longitudinal member.

19. The apparatus of claim 16, wherein said inner member is selected from the group consisting of: concentric rings, symmetric opposing slots, and a spring-shape mechanism.

20. The apparatus of claim 16, wherein said inner member and said outer hollow flexible longitudinal member comprise any of a circular, oval, rectangular, square, and triangular configuration, and wherein said outer hollow flexible longitudinal member is at least as long as said inner member.

* * * * *